US008115920B2

(12) United States Patent
Zhang et al.

(10) Patent No.: US 8,115,920 B2
(45) Date of Patent: Feb. 14, 2012

(54) METHOD OF MAKING MICROARRAYS

(75) Inventors: Jun-Ying Zhang, Woodbury, MN (US);
Terry L. Smith, Roseville, MN (US);
Haiyan Zhang, Woodbury, MN (US);
Jerome C. Porque, Bridgewater, NJ (US); Ding Wang, Austin, TX (US);
John C. Hulteen, Afton, MN (US); Lisa A. Dick, Afton, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 582 days.

(21) Appl. No.: 12/246,514

(22) Filed: Oct. 7, 2008

(65) Prior Publication Data

US 2009/0122310 A1    May 14, 2009

Related U.S. Application Data

(60) Provisional application No. 60/987,902, filed on Nov. 14, 2007.

(51) Int. Cl.
*G01J 3/44* (2006.01)
*G01N 21/65* (2006.01)

(52) U.S. Cl. ....................................... 356/301
(58) Field of Classification Search .................... 356/301
See application file for complete search history.

(56) References Cited

U.S. PATENT DOCUMENTS

| 4,689,291 A * | 8/1987 | Popovic et al. ............... 430/321 |
| 5,300,263 A | 4/1994 | Hoopman et al. |
| 5,709,943 A * | 1/1998 | Coleman et al. ............... 428/378 |
| 5,851,674 A | 12/1998 | Pellerite et al. |
| 6,301,051 B1 | 10/2001 | Sankur |
| 6,696,157 B1 | 2/2004 | David et al. |
| 6,700,708 B2 | 3/2004 | Houlihan et al. |
| 6,824,882 B2 | 11/2004 | Boardman et al. |
| 6,998,068 B2 | 2/2006 | Gerlach |
| 7,038,856 B2 | 5/2006 | Quake et al. |
| 7,042,645 B2 | 5/2006 | Houlihan et al. |
| 7,057,832 B2 | 6/2006 | Wu et al. |
| 7,109,519 B2 | 9/2006 | Gerlach |
| 7,173,778 B2 | 2/2007 | Jing et al. |
| 7,179,728 B2 * | 2/2007 | Kaneko et al. ............... 438/492 |

(Continued)

FOREIGN PATENT DOCUMENTS

JP     11-119004     * 4/1999

(Continued)

OTHER PUBLICATIONS

Baker, Highly Corrected Close-Packed Mircolens Arrays and Moth-Eye Structuring on Curved Surfaces, Appl. Opt. 38(2), (1999) pp. 352-356.

(Continued)

*Primary Examiner* — F. L. Evans
(74) *Attorney, Agent, or Firm* — Bradford B. Wright; Stephen F. Wolf

(57) ABSTRACT

Provided is a method of making microarrays that includes providing a substrate with discrete first microfeatures that have a first profile, and depositing vapor-coated materials onto the first microfeatures to form second microfeatures having a second profile that is substantially different from the first profile. Also provided is a method of adding a replication material to the vapor-coated microfeatures to form a mold. Microarrays made by this method can be used as substrates for surface-enhanced Raman spectroscopy (SERS).

11 Claims, 7 Drawing Sheets

U.S. PATENT DOCUMENTS

| | | | |
|---|---|---|---|
| 7,211,679 | B2 | 5/2007 | Gerlach et al. |
| 7,233,445 | B2 | 6/2007 | Nakajima |
| 7,315,042 | B2 | 1/2008 | Gerlach et al. |
| 2003/0059820 | A1* | 3/2003 | Vo-Dinh .......................... 435/6 |
| 2005/0048288 | A1 | 3/2005 | Flynn et al. |
| 2005/0214661 | A1 | 9/2005 | Stasiak et al. |
| 2005/0248848 | A1 | 11/2005 | Whitehead et al. |
| 2006/0105199 | A1 | 5/2006 | Gerlach et al. |
| 2007/0015288 | A1 | 1/2007 | Hulteen et al. |
| 2007/0134784 | A1 | 6/2007 | Halverson et al. |
| 2007/0172582 | A1 | 7/2007 | Mahoney et al. |
| 2007/0232781 | A1 | 10/2007 | Zhu et al. |
| 2007/0249802 | A1 | 10/2007 | Zhu et al. |
| 2008/0315459 | A1 | 12/2008 | Zhang et al. |
| 2009/0041986 | A1 | 2/2009 | Zhang et al. |
| 2009/0061039 | A1 | 3/2009 | Zhang et al. |
| 2009/0114618 | A1 | 5/2009 | Zhang et al. |

FOREIGN PATENT DOCUMENTS

WO    WO 2004/092836 A1    10/2004

OTHER PUBLICATIONS

Bhattacharya et al., IEEE Journal of Microelectromechanical Systems 14 (2005) pp. 590-597.

Brueck, Optical Interferometric Lithography-Nanotechnology Enablers, Proceedings of the IEEE, vol. 93 (10), Oct. 2005, pp. 1704-1721.

Cayre et al., Fabrication of Microlens Arrays by Gel Trapping of Self-Assembled Particle Monolayers at the Decane-Water Interface, Journal of Materials Chemistry, vol. 14, pp. 3300-3302, 2004, pp. 3300-3302.

Chari et al., Enhanced Outcoupling of Light From Organic Light-Emitting Diodes by Microlens Arrays Based on Breath-Figure Template, SID 07 Digest, 2007, pp. 852-855.

Christensen, Waveguide Excimer Laser Fabrication of 3D Microstructures, Proc. SPIE—Int. Soc. Opt. Eng., 2045 (1994) pp. 141-145.

Dieringer et al., Surface Enhanced Raman Spectroscopy: New Materials, Concepts, Characterization Tool and Applications, Paper 132, The Royal Society of Chemistry 2005, www.rsc.org/faraday_d, pp. 9-26.

Fu et al., Investigation of Diffractive-Refractive Microlens Array Fabricated by Focused Ion Beam Technology, Opt. Eng. 40(4), pp. 511-526, 2001.

Fu et al., Investigation of Integrated Diffractive/Refractive Microlens Microfabricated by Focused Ion Beam, Rev. Sci. Instrum. 71(6), (2000) pp. 2263-2266.

Gimkiewicz et al., Fabrication of Microprisms for Planar Optical Interconnections by Use of Analog Gray-Scale Lithography With High-Energy-Beam-Sensitive Glass, Appl. Opt. 38(14) (1999), pp. 2986-2990.

Guo et al., Micro Lens Fabrication by Means of Femtosecond Two Photon Photopolymerization, Optics Express, vol. 14, No. 2, 2006, 7 pages.

Helt et al., A Benchtop Method for the Fabrication and Patterning of Nanscale Structres on Polymers, Journal of the American Chemical Society, American Chemical Society, Was DC, vol. 126, No. 2, 2004, pp. 628-634.

Higglns et al., Nature, 404, 476 (2000) Anisotropic Spinodal Dewetting as a Route to Self-Assembly of Patterned Surfaces, pp. 476-478.

Jiang et al., Fabrication of Microlens in Photosensitive Hybrid Sol-Gel Films Using a Gray Scale Mask, Materials Science and Engineering C16, pp. 99-102, 2001.

Kudryashov et al., A New 2D to 3D X-Ray Lithography Technology for Gray Scale Structures, Microelectron Eng., 57-58 (2001) pp. 819-823.

Lee et al., A Simple Method for Microlens Fabrication by the Modified LIGA Process, Journal of Micromechanics and Microengineering, vol. 12, pp. 334-340, 2002.

MacFarlane et al., Microjet Fabrication of Microlens Arrays, IEEE Photonics Technology Letters, vol. 6, No. 9, 1994, pp. 1112-1114.

Naessens et al., Microlens Fabrication in PMMA With Scanning Excimer Laser Ablation Techniques, Proceedings Symposium IEEE/LEOS Benelux Chapter, 2000, Delft, The Netherlands, pp. 99-102.

Popovic et al., Technique for Monolithic Fabrication of Microlens Arrays, Applied Optics, vol. 27, No. 7 1988, pp. 1281-1284.

Radtke et al., Laser Lithographic Fabrication and Characterization of a Spherical Artificial Compound Eye, Optics Express, vol. 15, No. 6, 2007, 11 pages.

Ringe et al., Nanoscaled Surface Stuctures of Ionic Crystals by Spinodal Composition, Solid State Ionics, 177, (2006), pp. 2473-2479.

Shen, A Novel Fabrication for Mold Insert of Injection Molded Microlens Array, Materials Science Forum, vol. 532-533, pp. 665, 2006.

Shin et al., A New Approach to Polymeric Microlens Array Fabrication Using Soft Replica Molding, IEEE Photonics Technology Letters, vol. 16, No. 9, 2004, pp. 2078-2080.

Van Duyne et al., Atomic Force Microscopy and Surface-Enhanced Raman Spectroscopy. I. AG Island Films and AG Film Over Polymer Nanosphere Surfaces Supported on Glass, J. Chem Phys. 99 (1993) 2101-2115.

Wiltzius et al., Phys. Rev. A., 36(6), 2991, (1987) Structure of Porous Vycor Glass, pp. 2991-2994.

Wu et al., Fabrication of Arrays of Two-Dimensional Micropatterns Using Microspheres As Lenses for Projection Photolithography, Applied Physics Letters, vol. 78, No. 16, 2000, pp. 2273-2275.

Yabu et al., Simple Fabrication of Micro Lens Arrays, Langmuir, vol. 21, pp. 1709-1711, 2005.

Yaegashi et al., Direct Fabrication of Microlens Arrays With Polarization Selectivity, Advanced Materials, vol. 19, 2007, pp. 801-804.

Yang, Microcavity Top—Emitting OLEDs Integrated With Microlens Arrays: Simultaneous Enhancement of Quantum Efficiency, cd/A Efficiency and Color Performances, SID 70 Digest, 59.4, 2007, pp. 1698-1700.

Yoon et al., Multilevel/Microstructure Fabrication Using Single-Step 3D Photolithography and Single-Step Electroplating, SPIE- Int. Soc. Opt. Eng., 3512 (1998), pp. 358-366.

* cited by examiner

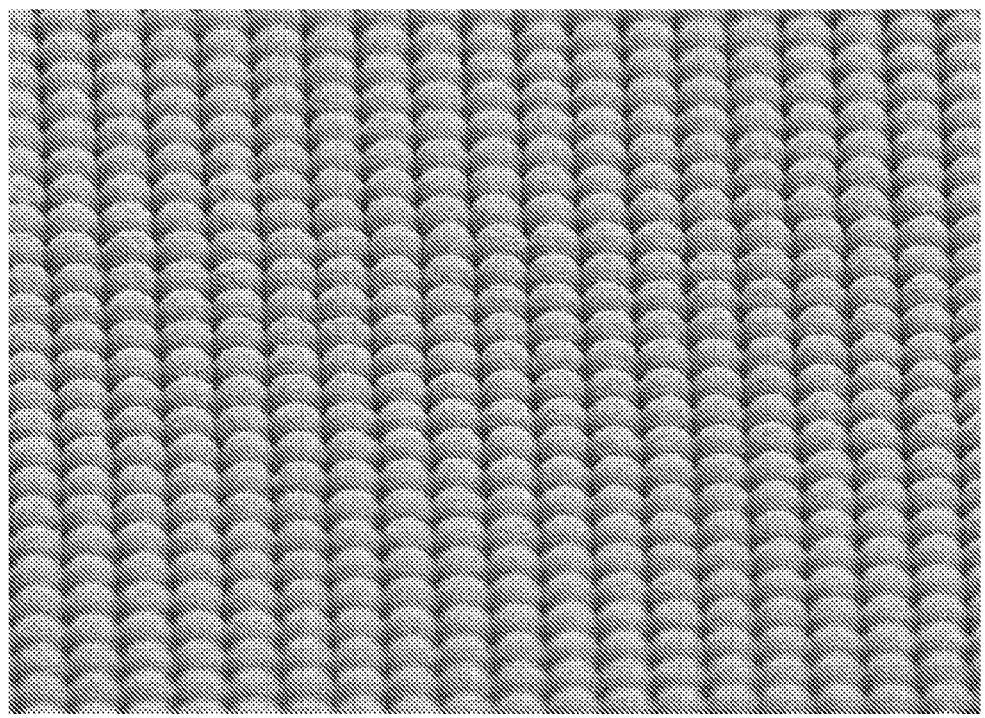
*Fig. 4A*  2 μm
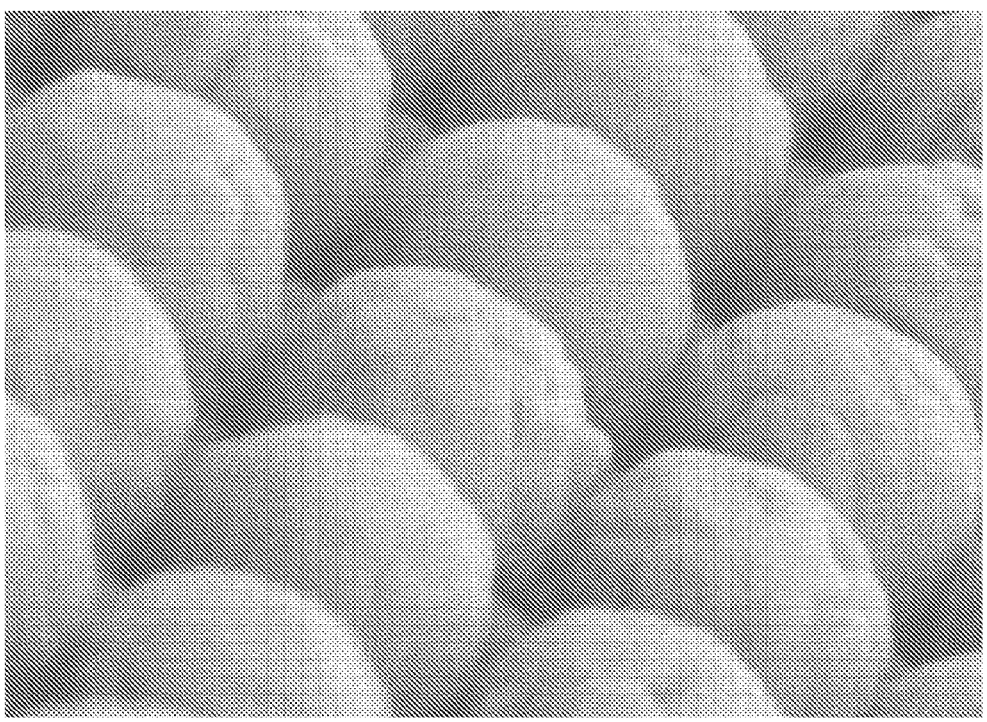
*Fig. 4B*  300 nm

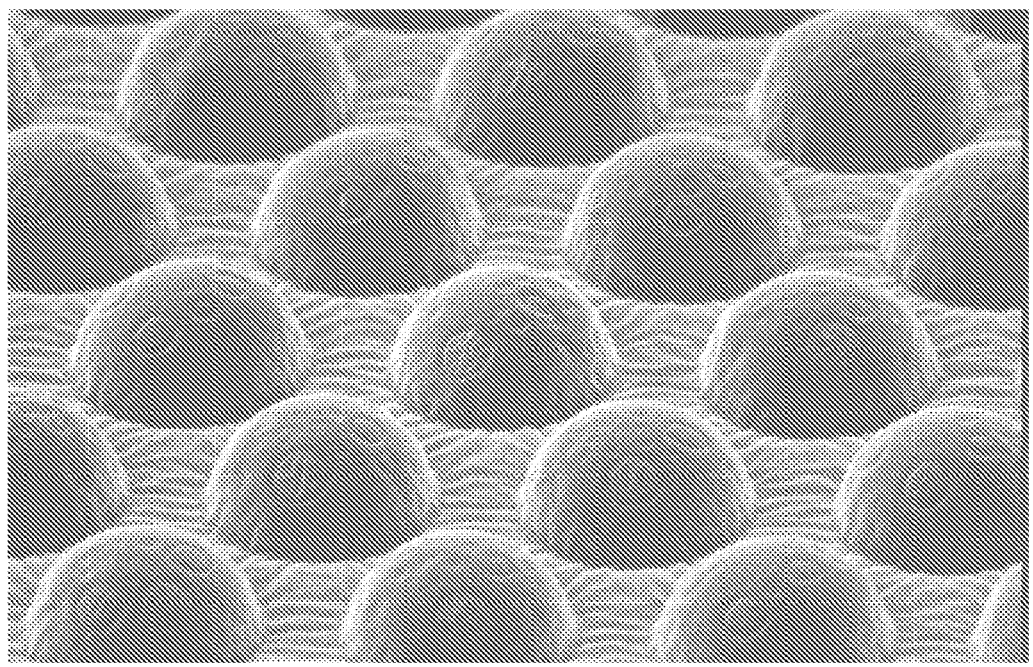
*Fig. 5A*  1 μm
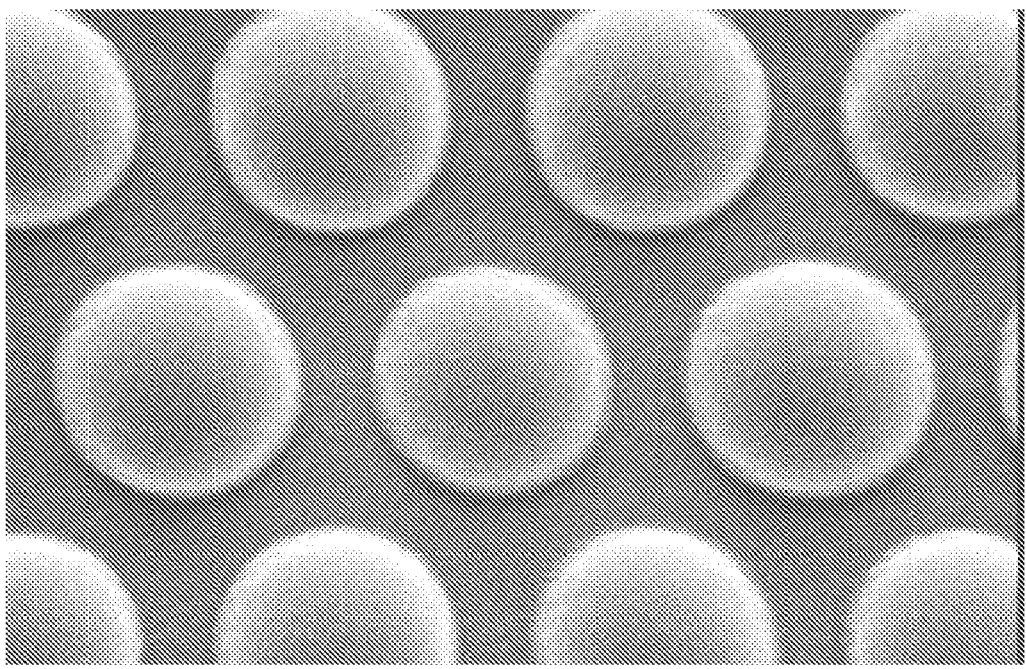
*Fig. 5B*  1 μm

METHOD OF MAKING MICROARRAYS

RELATED APPLICATIONS

This application claims priority to U.S. Provisional Application No. 60/987,902, filed on Nov. 14, 2007, which is incorporated herein by reference in its entirety.

BACKGROUND

There is an interest in commercial and industrial applications to reduce the size of articles and devices. This is particularly true in the area of electronics where devices have been made smaller and smaller. Microstructured and nanostructured devices, for example, can be used in articles such as flat panel displays, chemical sensors, and bioabsorption substrates. Microstructured articles (that have microfeatures) have found commercial utility in, for example, electroluminescent devices, field emission cathodes for display devices, microfluidic films, and patterned electronic components and circuits. Microstructured articles that are of interest include arrays of microspheres or microlenses on a substrate material. These can be used, for example, to create lenses, virtual images on signs, or substrates for analytical techniques that employ surface plasmon resonance for detection—for example, in surface-enhanced Raman spectroscopy.

SUMMARY

There is a need for generating arrays of microfeatures using low-cost manufacturing techniques. Manufacturing techniques that are low-cost include techniques that allow replication of a master mold. To further save cost and improve speed, the replication can be done on a roll-to-roll manufacturing line. The provided method involves applying a coating over an array of discrete microfeatures to create an array with microfeatures that are different from the original microfeatures. These different microfeatures can include, for example, spherical, spheroidal, and cylindrical profiles.

In one aspect, provided is a method of making an array that includes providing a plurality of discrete microfeatures on a substrate, wherein each of the first microfeatures has a first profile, and depositing material on the first microfeatures to form second microfeatures having a second profile that is substantially different from the first profile, wherein at least one of the second microfeatures does not comprise a substantially planar surface.

In another aspect, provided is a method of making an array that includes providing a plurality of discrete first microfeatures on a substrate, wherein each of the first microfeatures has a first profile, depositing material on the first microfeatures to form second microfeatures having a second profile that is substantially different from the first profile, wherein at least one of the second microfeatures does not comprise a substantially planar surface, adding a first replication material to the second microfeatures having a second profile, and separating the first replication material from the second microfeatures to form a mold.

In yet another aspect, provided is a mold that includes a plurality of discrete first microfeatures on a substrate, wherein each of the first microfeatures has a first profile, and material on the first profile of each of the first microfeatures that forms second microfeatures having a second profile that is substantially different from the first profile, wherein at least one of the second microfeatures does not comprise a substantially planar surface.

In this document the articles "a", "an", and "the" are used interchangeably with "at least one" to mean one or more of the elements being described;

"microstructure" or "microstructures" refer to structures that range from about 0.1 microns to about 1000 microns in their longest dimension. In this application, the ranges of nanofeatures and microstructures overlap;

"nanofeature" or "nanofeatures" refer to features that range from about 1 nm to about 1000 nm in their longest dimension. The nanofeatures of any article of this application are smaller than the microstructure generated on the article;

"pattern" or "patterns" refer to a configuration or configurations that can include regular arrays or random arrays of features or structures or a combination of both;

"profile" refers to an outline of an object, such as a microfeature, and is primarily a representation of the object as viewed from the side;

"resist" refers to a layer or layers of material that is placed on the substrate to selectively allow an etching agent to pass through in a patterned manner; and "spheroid" or spheroidal" refers to shapes that are like a sphere but not perfectly round and can have a profile of an arc of a circle or of an ellipse.

Provided are methods of making arrays with microfeatures that can be accomplished using low-cost manufacturing techniques, such as on a roll-to-roll manufacturing line. The methods can provide arrays that include microfeatures that can have spherical, spheroidal, and cylindrical features. The arrays made by the provided methods can be used, for example, as microlens arrays for optical applications, as substrates for analysis that relies upon the surface plasmon effect (such as surface-enhanced Raman spectroscopy (SERS), surface-enhanced fluorescence, or other surface-enhanced optical techniques), and to produce microfluidic arrays for biological applications. The methods provided herein include forming a mold and using the mold to form multiple replicas. The provided replicas can be used for the same applications as the original array.

The details of one or more embodiments are set forth in the accompanying drawings and description below. Other features, objects, and advantages will be apparent from the description and drawings, and from the claims.

BRIEF DESCRIPTION OF THE DRAWINGS

FIGS. 4A and 4B are photomicrographs of the microarray made as Example 1.

FIGS. 5A and 5B are photomicrographs of the polydimethylsiloxane (PDMS) replica of Example 4.

DETAILED DESCRIPTION

Figure 1A:
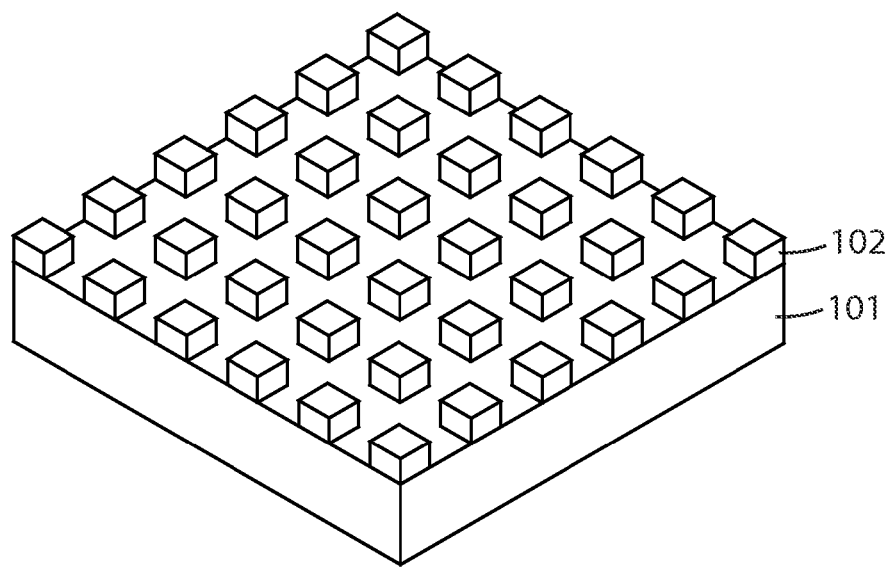
FIGS. 1A and 1B are drawings of embodiments of a substrate that include a plurality of discrete microfeatures.

The recitation of numerical ranges includes all numbers subsumed within that range (e.g., 1 to 5 includes 1, 1.5, 2, 2.75, 3, 3.80, 4, and 5). All numbers are herein assumed to be modified by the term "about".

This disclosure provides a method of making an array that includes providing a substrate that includes a plurality of discrete first microfeatures, wherein each of the first microfeatures has a first profile. The substrate can be selected from a variety of materials. These materials include polymeric films such as, for example, polyimide or polymethylmethacrylate, or inorganic materials such as glasses, silicon wafers, and coated silicon wafers. The coated silicon wafers can include wafers that have polymer film coatings such as, for example, polyimides or urethane acrylates, or can include inorganic coatings such as, for example, an $SiO_2$ coating. Additionally the substrate can be a porous glass as disclosed by Wiltzius et al., *Phys. Rev. A.*, 36(6), 2991, (1987) entitled "Structure of Porous Vycor Glass"; a polymer surface dewetted by a thin polymer film as described by Higgens et al., *Nature*, 404, 476 (2000) entitled "Anisotropic Spinodal Dewetting As a Route to Self-assembly of Patterned Surfaces", a mixed ionic crystal such as described in Ringe et al, *Solid State Ionics*, 177, 2473 (2006) entitled "Nanoscaled Surface Structures of Ionic Crystals by Spinodal Composition", or a light sensitive substrate. Light sensitive substrates can include photosensitive polymers, ceramics, or glasses.

The substrate can include a plurality of discrete first microfeatures. The discrete first microfeatures can be in a pattern. The pattern can form an array. It is to be herein understood that the term "microfeatures" includes features that can be on the order of microns (from about 1 µm to about 1000 µm or even larger) and also features that can be on the order of nanometers (from about 1 nm to about 1000 nm). This dimension is the average smallest dimension of the features in the array and can be the diameter, for example, if the features are cylindrical posts. The first microfeatures of this disclosure can have a maximum width (average smallest dimension) of less than 1000 µm, less than 500 µm, less than 100 µm, less than 10 µm, less than 1 µm, less than 0.1 µm (100 nm), or even less. The array can include a regular (repeating) arrangement of microfeatures, a random arrangement of microfeatures, a combination of different regular or random arrangements of microfeatures, or any arrangement of microfeatures. The array can include a singular microfeature. The microfeatures can be discrete or separate features. The pattern that includes microfeatures can be formed directly in the substrate or in an added layer. Additionally, the pattern can be formed as a part of the substrate.

The discrete first microfeatures can include microposts and microridges. Exemplary microposts can have one dimension (z-dimension) substantially perpendicular to the substrate referred to herein as the height, and two much smaller dimensions (x and y-dimensions). The smaller of the x-dimension and y-dimension is herein referred to as the width of the microfeature. For example, the cross-section (or base) of the microposts can be circular where the x-dimensions and the y-dimensions are equal. When the cross-section is circular and does not vary along the z-direction the microposts are cylinders. It is also possible that the x and y dimensions are equal but vary along the z-direction. In this case the microposts are conical. In another example, the cross-section of the microposts can be an ellipse. It is also contemplated, for example, that the microposts can have a cross-section of a polygon such as a triangle, square, pentagon, etc. If the cross-section of the micropost does not vary along the z-direction, the microposts can have the shape of a prism. In fact, any shape of micropost is contemplated by this disclosure as long as the micropost has one long dimension.

The pattern of microfeatures can be formed directly in the substrate. The pattern can be generated using patterning techniques such as anodization, photoreplication, laser ablation, electron beam lithography, nanoimprint lithography, optical contact lithography, projection lithography, optical interference lithography, and inclined lithography. The pattern can then be transferred into the substrate by removing existing substrate material using subtractive techniques such as wet or dry etching, if necessary. The pattern can be transferred into the substrate by wet or dry etching of a resist pattern. Resist patterns can be made from a variety of resist materials including positive and negative photoresists using methods known by those skilled in the art. Wet etching can include, for example, the use of an acid bath to etch an acid-sensitive layer or the use of a developer to remove exposed or unexposed photoresist. Dry etching can include, for example, reactive ion etching, or ablation using a high energy beam such as, for example, a high energy laser, or ion beam.

Alternatively, a layer or layers of nanoparticles coated on the top of the substrate can act as a resist pattern by preventing exposure of the substrate to radiation or etching where the nanoparticles reside, but allowing exposure of the resist in the areas not in direct line of the nanoparticles. This method is disclosed, for example, in Applicants' copending applications, U.S. patent application Ser. Nos. 11/766,561 and 11/766,412 (both Zhang et al.) which are herein incorporated by reference.

It is also contemplated that the pattern of first microfeatures can be formed on the substrate by coating the substrate with metal such as, for example, gold, silver, aluminum, chromium, nickel, titanium, or copper, annealing the metal to form islands of metal and then using the islands of metal as an etch mask for the substrate itself. Etching of the substrate can be accomplished with any of the etching techniques mentioned earlier in this application. It is also within the scope of this disclosure to form the pattern of first microfeatures using chromonics as disclosed, for example, in U.S. Pat. Publ. No. 2007/0172582 A1 (Mahoney et al.), which is incorporated herein by reference, as an etch mask.

The pattern of first microfeatures can also be formed by direct modification of the substrate without the addition of any material. For example, laser ablation can remove selected areas of the substrate to form first microfeatures. If the substrate is light-sensitive then it can be possible to form the pattern of first microfeatures by exposing the photosensitive substrate by optical projection or contact lithography and then developing. Alternatively, interference photolithography can be used to generate a pattern of first microfeatures in a photosensitive material.

A pattern of first microfeatures can be formed directly in the substrate by using a high energy beam to ablate the substrate. The pattern can be defined by rastering the beam, or by using an etch mask to protect parts of the substrate. The etch mask can be formed, for example, from an etch resist. This approach can be particularly useful for forming patterns of first microfeatures subtractively in some polymer substrates such as, for example, polyimide.

The pattern of first microfeatures can also be formed by adding a material to the substrate. The material can include the pattern of first microfeatures when it is added to the substrate, or the material can be added to the substrate and then subsequently have the pattern of first microfeatures generated in it. The pattern of first microfeatures can be formed in the material before it is added to the substrate. The pattern of first microfeatures can be added to the material subtractively using the methods herein. The pattern of first microfeatures can also be cast into the added material. For example, a replica with a negative relief article of the pattern of first microfeatures can be used to form the pattern of first microfeatures in the material. In this case, the material can be a thermoplastic material that flows at a high temperature and then becomes solid at room temperature or at use temperature. Alternatively, the material can be a thermoset and can be cured using a catalyst, heat, or photoexposure depending upon its chemistry. When the material is added to the substrate it can be added as a solid. The material can be added to the substrate by lamination or by adding a thin adhesive material. Materials that can be used for this purpose include thermoplastic polymers that flow at elevated temperatures but not at lower temperatures such as room temperature. Examples of thermoplastic polymers that can be used include acrylics; polyolefins; ethylene copolymers such as polyethylene acrylic acid; fluoropolymers such as polytetrafluoroethylene and polyvinylidene fluoride; polyvinylchloride; ionomers; ketones such as polyetheretherketone; polyamides; polycarbonates; polyesters; styrene block copolymers such as styrene-isoprene-styrene; styrene butadiene-styrene; styrene acrylonitrile; and others known to those skilled in the art. Other useful materials for forming a substrate with first microfeatures include thermosetting resins such as, for example, polydimethylsiloxanes, urethane acrylates and epoxies. An example of thermosetting resins can be a photocrosslinkable system, such as a photocurable urethane acrylate, that forms a polymeric substrate with microfeatures upon curing.

When addition of a material to the substrate is used to produce the pattern of first microfeatures, a number of materials can be used. For example, a photoresist (negative or positive) can be added to the substrate. The photoresist can be exposed to light passing through a photomask or projected through a lens system to produce the first microfeatures. Additionally interference lithography can be used to produce the pattern of first microfeatures. Interference lithography is discussed, for example, in S. R. J. Brueck, "Optical and Interferometric Lithography-Nanotechnology Enablers", *Proceedings of the IEEE, Vol.* 93 (10), October 2005. The exposed (positive photoresist) or unexposed (negative photoresist) areas can then be removed by using a developing solution to dissolve the undesired photoresist. The resist can then be hardened by physical or chemical means for use in later steps. It is also contemplated that the photoresist can be exposed by directly writing with a rastered or digitally-pulsed laser beam, as is known in the art. The developed photoresist can then be hardened and used as described herein. Useful photoresists include negative photoresists such as UVN 30 (available from Rohm and Haas Electronic Materials, Marlborough, Mass.), and FUTURREX negative photoresists (available from Futurrex, Franklin, N.J.), and positive photoresists such as UV5 (available from Rohm and Haas Electronic Materials) and Shipley 1813 photoresist (Rohm and Haas Electronic Materials). Other photopolymers can be used to generate the microfeatures. Any photopolymer system known to those skilled in the art can be used that can be used to form microfeatures upon exposure to radiation (UV, IR, or visible).

The resist pattern produced by exposure and development of the photoresist materials, can also be transferred into the substrate by direct removal of unwanted materials by dry etching using the photoresist as resist pattern. For example, reactive ion etching (RIE) can be used to remove parts of the substrate or materials added to the substrate in a manner so as to generate microfeatures. In reactive ion etching, a reactive gas species, such as $CF_4$ or $SF_6$ is added to a reaction chamber. A plasma is generated by applied radio frequency (RF) potentials. This causes some of the gas molecules to be ionized. These ionized particles can be accelerated towards various electrode articles and can etch or dislodge molecules from the article they impinge upon. Typically, reactive ion etching is done through an etch mask or directly using a rastered or digitally controlled beam.

Alternatively, a thin metal layer can be deposited on the substrate, the photoresist can be deposited on the metal, and the photoresist can be patterned, then the resist pattern can be transferred into the metal by wet etching. In this way a metal pattern can be generated that can serve as a resist pattern for dry etching of the substrate. Consequently a large etch rate difference between the (metal) resist pattern and the substrate can be achieved.

Each of the first microfeatures has a first profile. In some embodiments, the profile can be substantially linear. In other embodiments, the linear profile can be essentially parallel to the substrate and can constitute the outline of a plateau above the surface of the substrate. In yet other embodiments, the sides of the first profile can also be linear and, in some cases, can be at substantially at right angles to the outline of the plateau. Alternatively, the sides of the first profile can be curved. In many embodiments, the first profile has sharp angles.

The first microfeatures are discrete. For example, they can be in the form of microposts such as those depicted in FIG. 1A, in the form of microridges such as those depicted in FIG. 1B, or any other arrangements that form a pattern. Each first microfeature projects in a dimension away from or perpendicular to the substrate which is usually, but not always, substantially planar. By substantially planar it is meant that the substrate is more or less flat and usually defines a plane.

The method of making an array also includes depositing a material on the first microfeatures to form second microfeatures having a second profile that is substantially different from the first profile. Vapor-coated material can be deposited onto the first microfeatures by methods well know by those skilled in the art. Included in these methods, for example, are evaporation, sputtering, chemical vapor deposition (CVD), plasma-enhanced chemical vapor deposition (PECVD), and the like. Exemplary vapor-coated materials contemplated by this disclosure include conductors such as metals, metal oxides and organic conductors, insulators (dielectrics), semiconductors, and polymers. Conductive metals or metal oxide materials include silver, gold, aluminum, copper, indium tin oxide, and/or other materials. Organic conductors include, but are not limited to materials such as poly(3,4-ethylenedioxythiophene) (PEDOT), and polyaniline. Insulators include $SiO_2$, SiN, and $Al_2O_3$. Semiconductors can be organic such as, for example, organic semiconductors which may be used to form the active layer of the electronic devices. For example, a variety of organic semiconductors can be used including fused aromatic ring compounds as exemplified by small molecules such as pentacene-containing compounds, tetracene-containing compounds, anthracene-containing compounds, bis(acenyl)acetylene compounds, and acene-thiophene compounds. Several polymeric materials have also been considered such as regioregular polythiophenes exemplified by poly(3-alkylthiophene) and polymers having fused thiophene units or bis-thiophene units. Additional disclosures of organic semiconducting materials that can be useful in this application include the materials disclosed in U.S. Pat. Nos. 7,109,510 and 6,998,068 (both to Gerlach), U.S. Pat. Nos.

7,211,679 and 7,315,042 (Gerlach et al.), and U.S. Pat. Publ. Nos. 2007/0232781 and 2007/0249802 (both Zhu et al.).

The provided arrays include coated second microfeatures having a second profile that is substantially different from the first profile. By substantially different it is meant that the profile of the coated second microstructures (second profile) is not congruent with the first profile. Additionally the second profile does not have the essentially same shape or is not recognized to have essentially the same shape as the first profile. In some embodiments the second profile is curved or has a radius of curvature that is larger than that of the first profile. For example, the first profile can have rectangular features and the second profile can have curved (circular, elliptical, or otherwise) features. In other embodiments, the curve is circular or elliptical and is located where the plateau of the first profile was located before the deposition of material on the first profile. The curved profile can be concave or convex. Examples of convex curved profiles include the profiles of spherical surfaces and spheroidal surfaces (that are ellipsoidal). At least one of the first microfeatures can have a long dimension that is at least 5 percent, at least 8 percent, at least 10 percent, at least 15 percent, or even at least 20 percent of its smallest dimension.

At least one of the second microfeatures does not comprise a substantially planar surface. For example, at least one of the second microfeatures can have a spherical or spheroidal surface. In many embodiments, most, if not all of the second microfeatures do not comprise a substantially planar surface. Spherical and spheroidal surfaces can be used as lens elements if they are transparent to actinic radiation. Thus, the provided method can be used to make microlens arrays. The provided method can be used to make an array of second microfeatures wherein the second microfeatures can include at least one convex curved surface where convex is defined as a structure that has a curvature in at least one transverse direction and a local center of curvature (focus) on the substrate side. In some embodiments, the array of features of this invention can also include at least one curved surface that is concave—for example, the surface can have a curvature in at least one transverse direction and a local center of curvature on the side away from the substrate. These arrays can be arrays of microspheroids (including, for example, microspheres). In other embodiments, the arrays can be arrays of microridges with spheroidal tops. If the curved surfaces on the microspheres are convex and are made of material transparent to visible radiation, the arrays can be arrays of microlenses. If the curved surfaces are made with or coated so that the surfaces are reflective to radiation, then the array of microspheroids can be an array of microlenses that focus (concave) or scatter (convex) the radiation by reflection. By varying the first profile of the microfeatures and/or the deposition process conditions (time, temperature, method), it has been found that the size, and shape of the second profile can be controlled.

An important aspect of the provided method and the arrays made therefrom is that the arrays are made by directly depositing material on the first microfeatures to form second microfeatures having a second profile wherein the second profile is substantially different from the first profile. Any curvature in the profile of the second microfeatures is imparted from the deposition of the material, vapor depositing as an example. No reflow or annealing of the second microfeatures is required in the provided method. This allows a method of making an array that can be done at lower temperatures than is normally used in reflowing materials such as glass and can accommodate substrates that are temperature sensitive such as polymers, for example poly(methyl methacrylate), PET, photoresists, etc Other embodiments of the provided method include the addition of a smoothing layer to the second microfeatures having a second profile. The smoothing layer can be added to the second microfeatures in order to reduce the amount of roughness of the surface of the microfeatures having a second profile. Materials that are suitable as smoothing layers include metals. The metals can include, for example, metals selected from aluminum, tin, nickel, gold, or silver. The thickness of the smoothing layer is enough to smooth out the roughness on the surface of the surface of the second microfeatures but is not thick enough to substantially change the second profile. The smoothing layer is nominally 500 nm or less.

In another aspect, provided is a method of making an array that includes providing a substrate comprising a plurality of discrete first microfeatures, wherein each of the first microfeatures has a first profile, depositing material on the first microfeatures to form second microfeatures having a second profile that is substantially different from the first profile, adding a first replication material to the second microfeatures having a second profile, and separating the first replication material from the array of second microfeatures to form a mold. Polymers useful as first replication materials can include thermoplastic polymers and thermosetting polymers known to those skilled in the art. Thermoplastic polymers can include materials that soften or melt above room temperature but that are rigid and can hold structure when at or below room temperature. Some thermoplastic polymers that can be useful to produce replicas include, for example, polymethylmethacrylate (PMMA), polycarbonate (PC), polystyrene (PS), polyvinylchloride (PVC), polypropylene (PP), polyethylene terephtalate (PET), polyetheretherketone (PEEK), polyamide (PA), polysulfone (PSU, very brittle polymer), polyvinylidenefluoride (PVDF), and polyoxymethylene (POM, very soft and elastic polymer).

Thermosetting polymers can also be useful as first replication materials. Thermosetting polymers that are useful include polysiloxanes (such as polydimethyldisiloxane (PDMS)), polyimides (made from curing of polyamic acid), and urethane acrylates. For the replication of nanofeatures and microstructures, the polymers used to form the replica can have low viscosity. Low viscosity polymers can allow into and around the microfeatures. It can be useful to apply the polymer to the article under vacuum so that air entrapment between the article and the polymer is minimized.

It can be advantageous to apply a release coating to the array before adding a first replication material to the mold. If plurality of discrete first microfeatures is made from $SiO_2$, SiN, or other inorganic or polymeric materials, the mold can be coated with a fluorosilane release agent such as, for example, trimethychlorosilane or fluorinated siloxanes such as those disclosed in U.S. Pat. No. 5,851,674 (Pellerite et al.). Also useful for this purpose are hexafluoropolyprolylene oxide (HFPO) derivatives such as those disclosed in U.S. Pat. No. 7,173,778 (Jing et al.). These disclosures are herein incorporated by reference.

Alternatively, the array of second microfeatures can be metallized with, for example, a thin layer of nickel that has been vapor deposited or deposited by electroless plating. If the article is metallized it can also be advantageous to put a release agent on the metallized article to enhance the release of the polymers that form the replica. For example, the array of microposts can be coated with a release layer such as a fluorinated phosphonic acid as disclosed in U.S. Pat. No. 6,824,882 (Boardman et al.) or perfluoropolyether amide-linked phosphonates such as those disclosed in U.S. Pat. Publ. No. 2005/0048288 (Flynn et al). It is also contemplated that the array of microposts can be protected by coating with diamond-like glass as disclosed, for example in U.S. Pat. No. 6,696,157 (David et al.). Other materials that can be used as a release layer are discussed in applicants' copending applications, U.S. Ser. No. 11/766,477 (Zhang et al.). These disclosures are hereby incorporated by reference.

The first replication materials can be placed in contact with the mold or the release layer, cured by any of a variety of means including heat, moisture or radiation, and then separated from the article to produce a negative relief image (replica) of the array. The replicas can be used to produce secondary or daughter molds of the original array of microposts.

Provided for is a mold that includes a substrate comprising a plurality of discrete first microfeatures, wherein each of the first microfeatures has a first profile, vapor-deposited material on the first microfeatures to form second microfeatures that have a second profile that is substantially different from the first profile. The mold can be made by the provided methods and can be used to make replicas as described above.

The replicas can be filled with a second replication material that can be any of the materials used as the first replication material. The second replication material can be cured and separated replica to form a secondary or daughter mold. It can be advantageous to add a release layer to the replica to enhance the ability to separate daughter mold from the replica. In this way many daughter molds can be made from one original mold. Release layers that can be used to enhance the separation of daughter molds from replicas when the replicas are made of PDMS include materials such as the release materials for the molds as well as perfluoroether silane release agents which are disclosed in U.S. Ser. No. 11/845,465 (Zhang et al.) which is incorporated herein by reference.

Figure 1B:
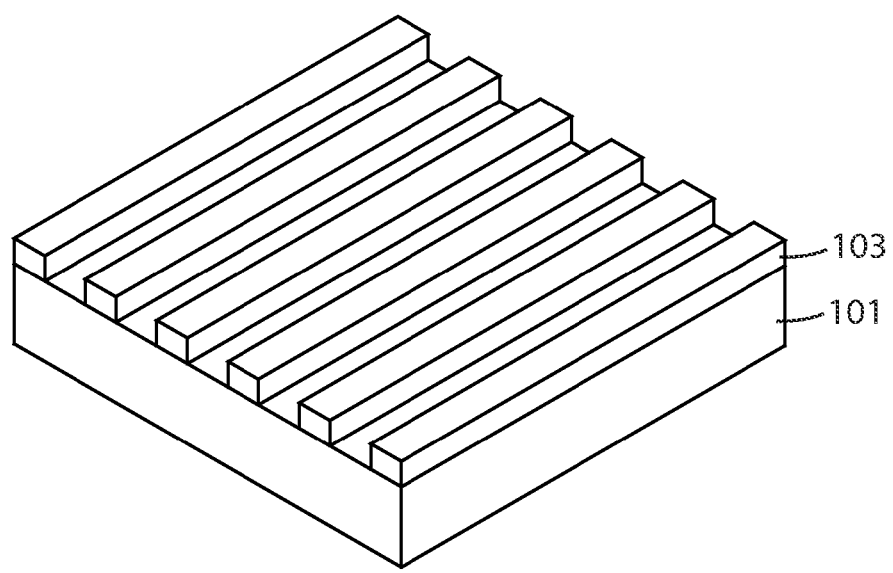
Figure 2A:
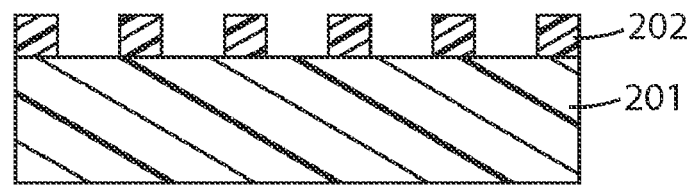
FIG. 2A is a drawing of a substrate with an array of microposts.
Figure 2B:
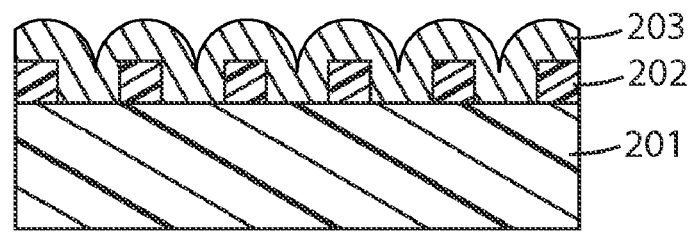
FIG. 2B is a drawing of an array of microposts with deposited material.
Figure 2C:
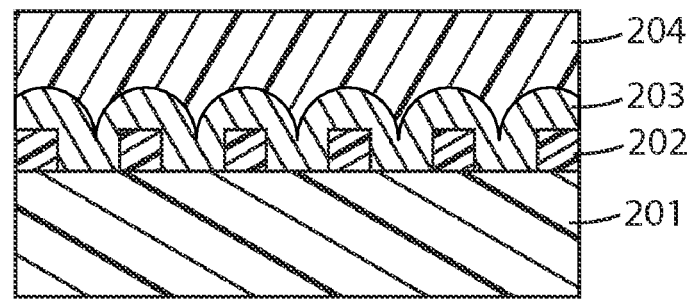
FIG. 2C is a drawing of the array of FIG. 2B with a first replication material over the microposts.
Figure 2D:
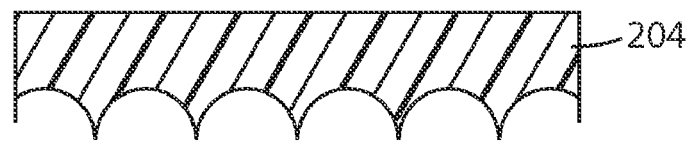
FIG. 2D is a drawing of a mold.
Figure 2E:
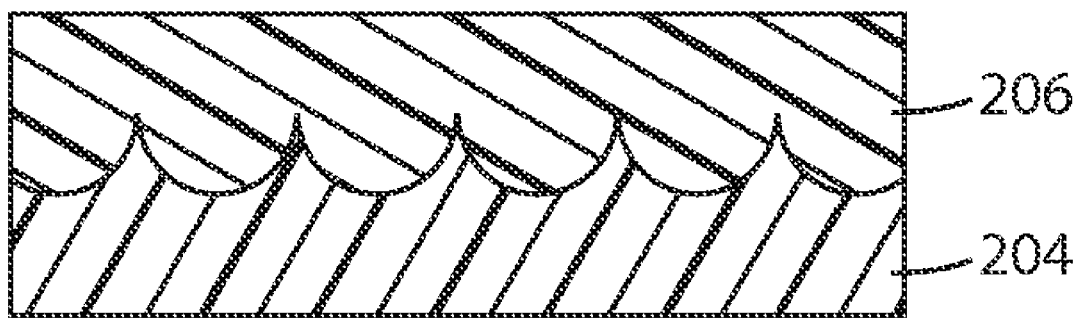
FIG. 2E is a drawing of a second replication material in contact with the mold of FIG. 2D.
Figure 2F:
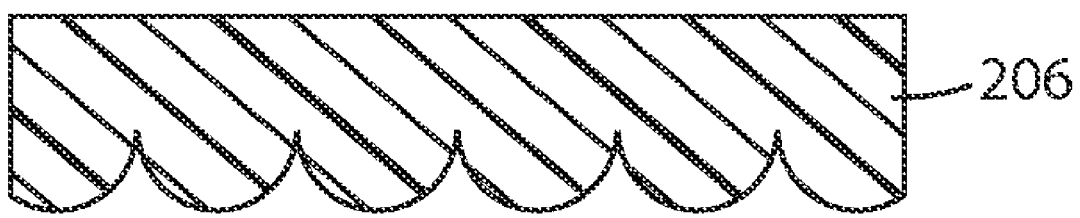
FIG. 2F is a drawing of the replica from FIG. 2E.
Figure 3A:
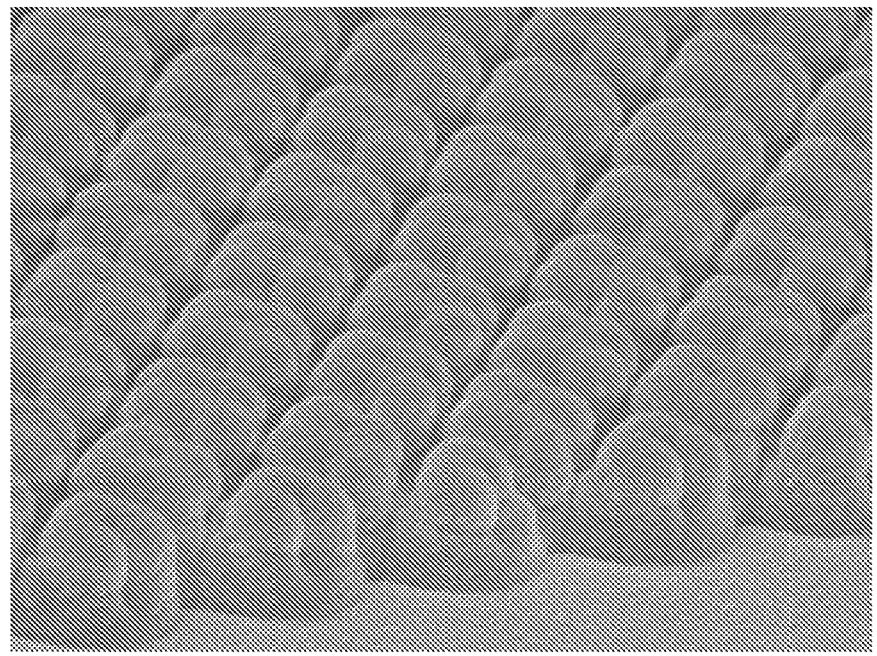
FIGS. 3A and 3B are photomicrographs of different embodiments of arrays made by the provided methods.
Figure 3B:
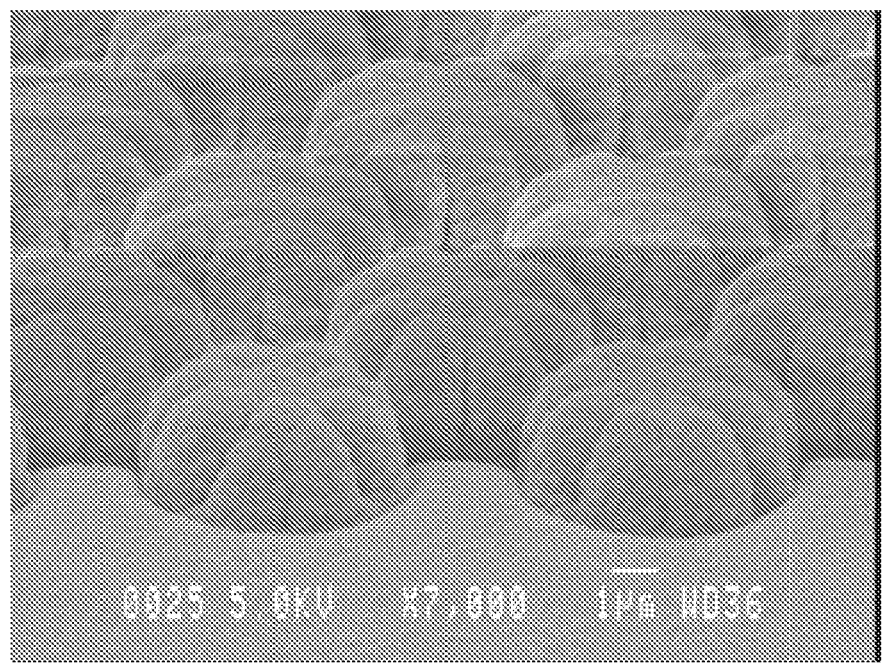

Some of the embodiments disclosed herein can be further understood by reference to the Figures. FIGS. 1A and 1B are drawing of two embodiments of substrate that include a plurality of discrete microfeatures. FIG. 1A shows a rectangular array of small microposts on a substrate. FIG. 1B shows an array of microridges. FIGS. 2A-2F illustrate one embodiment of the method of this disclosure. FIG. 2A is an array of microposts 202 atop a substrate 201. As discussed earlier there are a number of materials that can be useful for either the substrate 201 or the microposts 202. The profile of the array of microposts 202 is rectangular. FIG. 2B is a drawing of the array of microposts presented in FIG. 2A that has had a material 203 deposited on the microposts 202 to form an array of microposts that have a second profile that is substantially different than the first profile. In FIG. 2B the profile of the surfaces includes a circular portion. FIG. 2C is a drawing of the array of microposts that include at least one surface from FIG. 2B with first replication material 204 on top of the microsphere array. The first replication material can then be cured and separated from the array to form a mold 204 as shown in FIG. 2D. The mold 204 can then be filled with a second replication material 206 as shown in FIG. 2E to form, after curing the second replication material, a replica 206. Replica 206 is shown in FIG. 2F. FIGS. 3A and 3B are photomicrographs of two embodiments of molds that show that the provided method can be used to make complex spheroidal shapes.

Using the provided methods a variety of arrays can be made. For example, an array of microspheres in a variety of patterns can be constructed, molded, and replicated by the methods presented herein. By using an optically clear replication material the methods herein can provide for a microlens array. Optically clear replication materials can include visibly transmissive thermoset polymers such as, for example, acrylic polymers, polycarbonates, urethane acrylates, epoxies, etc. Optically transmissive thermoplastic materials can also be used to form microlens arrays. These materials can include, for example, polycarbonates, polymethylmethacrylates, polyolefins, polyethylene acrylic acids, polyvinyl chlorides, polyvinylfluorides, ionomers, ketones such as polyetheretherketone, polyamides, polyesters, styrene block copolymers and others known to those skilled in the art. The microlenses of the array can be spherical or spheroidal as discussed above. Arrays of microlenses can be useful, for example, in virtual imaging and other optical applications. Reflective microsphere arrays can be useful, for example, in surface-enhanced Raman spectroscopy (SERS) and other analytical techniques that use surface plasmon effects. The analytical techniques include a method of analysis that includes providing an array made by the provided methods wherein the arrays are reflective and include a metal layer, providing an analyte in close proximity to at least a portion of the metal layer, and performing surface-enhanced Raman spectroscopy on the analyte. The array can be an array made by any of the provided methods including original arrays or replicas. If the array is a replica and is made of a non-metal then the replica can be coated with a layer of metal before providing an analyte in close proximity to at least a portion of the metal layer. An analyte can be any material or mixture of materials that can be analyzed by SERS. This can include a variety of materials including, for example, organic compounds, mixtures of organic compounds, inorganic compounds, polymers, polymer/monomer mixtures, metals, alloys, organometallics, and biomolecules.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows. All references in this disclosure are herein incorporated by reference.

EXAMPLES

Example 1

Arrays of Microspheres from Overcoating Arrays of Nanoposts

An array of photoresist (PR) post structures was fabricated on Si wafers, glass, and plastic substrates by optical interference lithography using a 244 nm frequency doubled argon laser with an output of 300 mW (Sabre FreD Laser, available from Coherent Inc., Santa Clara, Calif.) in a positive photoresist (Shipley UV5 resist, available from Rohm and Haas Electronic Materials Inc., Marlborough, Mass.). The resulting array had post structures with a diameter of 240 nm and a pitch of 480 nm. The array of post structures was coated with 750 nm of material that included 110 nm indium-tin oxide (ITO) deposited by sputtering, 390 nm organic light emitting diode (OLED) deposited by evaporation, and 250 nm Al also deposited by evaporation. Very close packed microsphere structures were formed after the coating. FIG. 4A is a photomicrograph of the microsphere array of Example 1. FIG. 4B is a magnified image of a portion of the microsphere array. As can be seen, very close packed microsphere structures were formed. The size and shape of microsphere could be controlled by varying the initial post size, height, density or by the over-coating process parameters (see example 2 and 3).

Example 2

Arrays of Microspheres Created by PECVD and Si$_3$N$_4$ Overcoating on Nanopost Structures Photoresist (PR) post structures were fabricated on Si wafers, glass, and plastic substrates by optical interference lithography as described in Example 1. The resulting PR post structures with a diameter of 900 nm and a pitch of 1.6 um. A 750 nm thick layer of silicon nitride was coated onto the PR post structures by plasma-enhanced chemical vapor deposition (PECVD), Model PLASMALAB System 100, available form Oxford Instruments, Yatton, UK, using the following parameters described in Table 1.

TABLE 1

Conditions used for depositing Si$_3$N$_4$ layer

| Reactant/Condition: | Value: |
|---|---|
| SiH$_4$ | 300 sccm |
| NH$_3$ | 20 sccm |
| N$_2$ | 600 sccm |
| Pressure | 700 mTorr (93.3 Pa) |
| Temperature | 60° C. |
| High frequency (HF) power | 40 W |

After Si$_3$N$_4$ coating, it was observed that microlens-like structures were formed by the deposition of Si$_3$N$_4$ on the post structures by PECVD. Different shapes of microspheroids were formed by different deposition conditions.

Example 3

Fast Growth of SiO$_2$ on Posts Using PECVD

Example 3 demonstrates intentionally created nano-features (or roughness) on the microspherical surfaces. A photoresist (PR) post pattern was fabricated on a Si wafer by optical interference lithography as in Example 1. A 750 nm thick layer of silicon dioxide was coated onto the PR post structures by plasma-enhanced chemical vapor deposition (PECVD), this time using a fast deposition rate in order to create roughness on microsphere surface, The deposition parameters described in Table 2:

TABLE 2

Conditions used for depositing SiO$_2$ layer

| Reactant/Condition: | Value: |
|---|---|
| SiH$_4$ | 300 sccm |
| N$_2$O | 1600 sccm |
| N$_2$ | 600 sccm |
| Pressure | 1600 mTorr (213.3 Pa) |
| Temperature | 60° C. |
| High frequency (HF) power | 110 W |

It was observed that nanoscale roughness was formed on the micro-spherical surface by the fast deposition of the SiO$_2$ by PECVD process. The size of the nanofeatures on the microspheres was 0-100 nm.

Example 4

Microsphere PDMS Replica Made from PDMS Mold

A photoresist (PR) post pattern was fabricated on a silicon wafer by optical lithography. A 1500 nm thick layer of silicon dioxide, with fast deposition rate in order to create roughness on microsphere, was coated onto the PR post structures by PECVD, using the process parameters as in the Example 2.

Poly(dimethyl siloxane) (PDMS) (available as SYLGARD 184 Silicone Elastomer Kit, available from Dow Corning, Midland, Mich.) and its curing agent (available from Dow Corning, Midland, Mich.) were thoroughly mixed in a 10:1 weight ratio. Air bubbles trapped in the mixture were removed by degassing for 30 min at low vacuum. The degassed mixture was poured onto the SiO$_2$ over-coated PR pattern, and further degassed for another 30 min, before curing on a hot plate at 80° C. for 1 h. After curing, the PDMS replica was peeled off the SiO$_2$ over-coated PR master, yielding the desired PDMS mold with negative structures.

In order to make a PDMS replica of the PDMS mold, the mold was treated with release agent. Before coating the HFPO-silane release agent on the PDMS mold, an oxygen plasma treatment of the mold was carried out, using a reactive ion etching (RIE) system. The RIE was done using a Model PLASMA LAB System 100, available from Oxford Instruments, Yatton, UK.). The RIE treatment allowed the HFPO release agent to chemically bond to the mold surface, resulting in a self-assembled monolayer (SAM) serving as an anti-adhesion layer on the mold. The parameters used for O$_2$ plasma treatment of the mold are listed in Table 3:

TABLE 3

RIE Conditions

| RF power: | 200 W |
|---|---|
| Pressure: | 10 mTorr |
| ICP power: | 1500 W |
| O2: | 20 sccm |
| Time: | 8 s |

Following the plasma treatment, the mold was treated with HFPO by dipping the mold in a solution of 0.1 wt % HFPO in a mixture of methoxynonafluoroisobutane and methoxynonafluorobutane (HFE7100, available from 3M Company, St. Paul, Minn.) and heating the treated mold in an oven for 1 hour at 120° C. After the mold had cooled to room temperature it was rinsed for 1 minute with fresh HFE7100.

The degassed Sylgard 184 PDMS mixture described above was poured onto the PDMS mold, further degassed for another 30 min, and then cured on a hot plate at 80° C. for 1 hr. After curing, the PDMS replica was easily peeled off the PDMS mold. High-quality microsphere replicas of the mold were produced. FIGS. 5A and 5B are photomicrographs of the PDMS replica of Example 4 with FIG. 5A being a cross-sectional view at a 60 degree viewing angle and FIG. 5B is a top view of the same array.

Example 5

Nanosphere Arrays for Surface-Enhanced Raman Spectroscopy (SERS)

Figure 6:
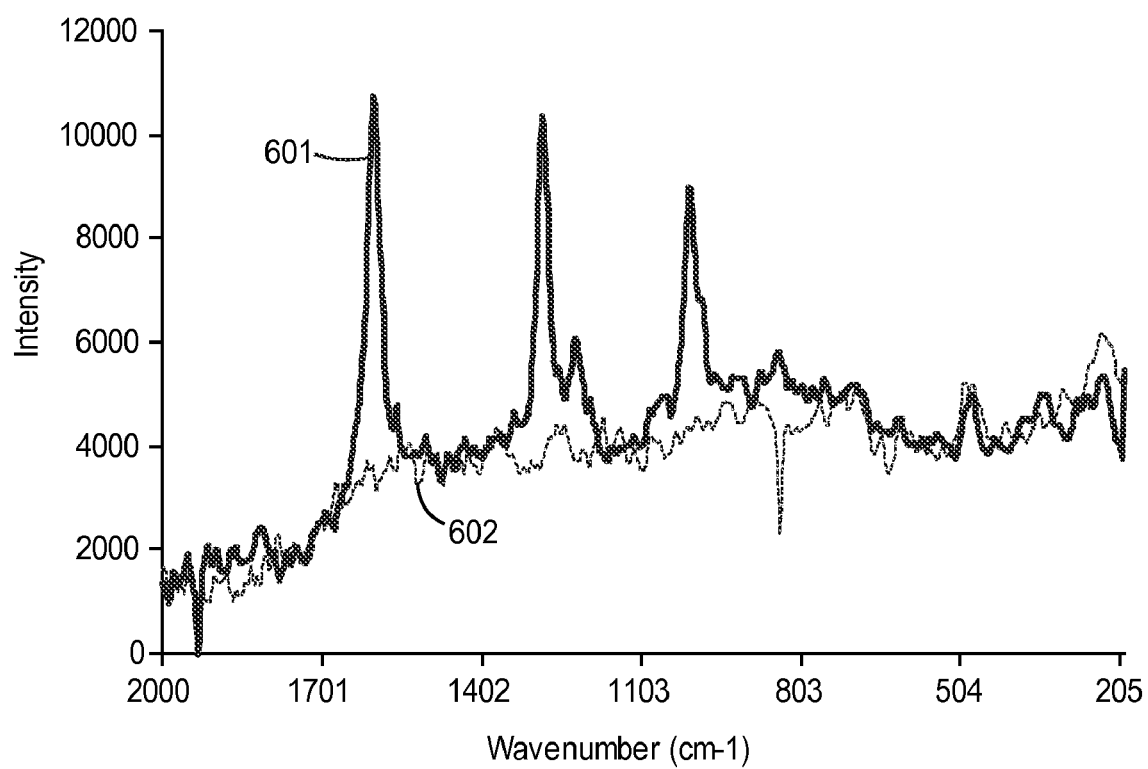
FIG. 6 is a SERS spectrum of bipyridine using the substrate in Example 5.

Surface-enhanced Raman spectra for bipyridine (BPY) were obtained on gold-coated array of nanospheres made by replication process from a mold in Example 1. BPY was ordered from Sigma-Aldrich (St. Louis, Mo.). The BPY was dissolved in a methanol solution with a concentration of 0.13 mM. One drop of the solution was then applied to the surface of the array. After spinning off extra solution, a thin coating of BPY remained on the surface of the array. An "Inspector Raman" made by DeltaNu (Laramie, Wyo.) was used to record the Raman scattering. The laser wavelength was 785 nm. Acquisition time was 10 second. The laser power was about 2.3 mW. The gathered spectrum (601 on FIG. 6.) showed the SERS peaks at 1001, 1291, and 1604 $cm^{-1}$ of BPY on the substrate consisting of gold-coated close packaged nanospheres. As a comparison, a gold-coated sample with no BPY was measured as the control and its SERS spectrum is also shown on FIG. 6 as 602. The three primary SERS peaks are not present in the control sample.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of making an array comprising:
   providing a plurality of discrete first microfeatures on a substrate, wherein each of the first microfeatures has a first profile;
   vapor depositing material on the first microfeatures to form second microfeatures having a second profile that is substantially different from the first profile, wherein the material comprises a first metal, and wherein at least one of the second microfeatures does not comprise a substantially planar surface; and
   adding a smoothing layer after depositing material.

2. The method according to claim 1 wherein the smoothing layer comprises a second metal.

3. The method according to claim 2 wherein the second metal is selected from aluminum, tin, nickel, gold, silver, and a combination thereof.

4. A method of making an array comprising:
   providing a plurality of discrete first microfeatures on a substrate, wherein each of the first microfeatures has a first profile;
   vapor depositing material on the first microfeatures to form second microfeatures having a second profile that is substantially different from the first profile, wherein the material comprises metal, and wherein at least one of the second microfeatures does not comprise a substantially planar surface;
   adding a first replication material to the second microfeatures having a second profile; and
   separating the first replication material from the second microfeatures to form a mold.

5. The method according to claim 4 further comprising adding a smoothing layer to the microfeatures having a second profile before the addition of the first replication material.

6. The mold made according to claim 4.

7. The method according to claim 4 further comprising:
   adding a second replication material to the mold; and
   separating the second replication material from the mold to form a replica.

8. The replica made according to the method of claim 7.

9. The replica according to claim 8 wherein the replica comprises a microlens array.

10. A method of analysis comprising:
    providing an array made by a method comprising:
      providing a plurality of discrete first microfeatures on a substrate, wherein each of the first microfeatures has a first profile;
      vapor depositing material on the first microfeatures to form second microfeatures having a second profile that is substantially different from the first profile, wherein the material comprises a first metal, and wherein at least one of the second microfeatures does not comprise a substantially planar surface;
    providing an analyte in close proximity to at least a portion of the array; and
    performing surface-enhanced Raman spectroscopy on the analyte.

11. A method of analysis comprising:
    providing a replica according to the method of claim 7
    coating the replica with a layer of metal to form a metallized array;
    providing an analyte in close proximity to at least a portion of the metallized array; and
    performing surface-enhanced Raman spectroscopy on the analyte.

* * * * *